(12) United States Patent
Kuo et al.

(10) Patent No.: US 7,514,465 B2
(45) Date of Patent: Apr. 7, 2009

(54) SYNTHESIS OF $N^2$-(SUBSTITUTED ARYLMETHYL)-3-(SUBSTITUTED PHENYL)INDAZOLES AS NOVEL ANTI-ANGIOGENIC AGENTS

(75) Inventors: Sheng-Chu Kuo, Taichung (TW); Li-Jiau Huang, Taichung (TW); Fang-Yu Lee, Taichung (TW); Che-Ming Teng, Taipei (TW); Mei-Ling Shih, Taichung (TW); Hua-Sin Chen, Taichung (TW)

(73) Assignee: Yung Shin Pharm. Ind. Co., Ltd., Taichung (TW)

( * ) Notice: Subject to any disclaimer, the term of this patent is extended or adjusted under 35 U.S.C. 154(b) by 543 days.

(21) Appl. No.: 11/274,528

(22) Filed: Nov. 15, 2005

(65) Prior Publication Data

US 2006/0106032 A1   May 18, 2006

Related U.S. Application Data

(60) Provisional application No. 60/628,266, filed on Nov. 16, 2004.

(51) Int. Cl.
*C07D 231/56* (2006.01)
*A61K 31/4162* (2006.01)

(52) U.S. Cl. .................................. 514/406; 548/361.1
(58) Field of Classification Search ........................ None
See application file for complete search history.

(56) References Cited

U.S. PATENT DOCUMENTS

| | | | |
|---|---|---|---|
| 6,518,294 | B2 | 2/2003 | Teng et al. |
| 6,887,997 | B2 | 5/2005 | Lee et al. |
| 2004/0167127 | A1 | 8/2004 | Steffan et al. |
| 2005/0215612 | A1 | 9/2005 | Kuo et al. |

FOREIGN PATENT DOCUMENTS

| | | |
|---|---|---|
| WO | WO 99/45007 A | 9/1999 |
| WO | WO 02/059110 A | 8/2002 |
| WO | WO 03/082274 A | 10/2003 |

OTHER PUBLICATIONS

Hetercycles, vol. 55, No. 9, pp. 1813-1816, (2001).*

Shih, Mei-Ling, "Synthesis, Antiplatelet, Antiangiogenesis and Cytotoxicity Activity of 1(or 2)-(Substituted benzyl)-3-(4-methylphenyl)-1(or 2)*H*-indazoles", China Medicinal College Master Thesis, Jul. 2002, pp. 16, 17, 22 and 38 (English translation attached).

Garcia, Maria Angeles et al., "Polymorphism vs. Desmotropy: The Cases of 3-Phenyl-and 5-Phenyl-1*H*-pyrazoles and 3-Phenyl-1 *H*-indazole", Helvetica Chemica Acta, vol. 85, 2002, pp. 2763-2776.

Radinov, Rumen et al., "3-Phenylpyrazolo(4,3-c)Pyridine and Derivatives: Structure Determination", Journal of Molecular Structure, 158 (1987), pp. 99-108.

Taylor, Edward C., "'Bicyclobenzodiazepinones' from 3-Oxo-1,2-diazetidinium Hydroxide, Inner Salts", Tetrahedron, vol. 47, No. 46, 1991, pp. 9599-9620.

Zenchoff, Gladys S. et al., The Synthesis of Indazoles via 2,3-Dihydroindazoles (1), Journal of Heterocyclic Chemistry, 13, 1976, pp. 33-39.

European Search Report; EP 05 02 4934, Jan. 30, 2006.

García, M. A.; López, C.; Claramunt, R. M.; Kenz, A.; Pierrot, M.; Elguero, J., "Polymorphism vs. Desmotrophy: The Cases of 3-Phenyl- and 5-Phenyl-1H-pyrazoles and 3-Phenyl-1H-indazole", Helvetica Chimica Acta, vol. 85, 2002, pp. 2763-2776.

V. Auwers, K.; Huttenes, K., "über 3-Pheyl-indazol und 2-Oxy-3-phenyl-indazol", Chemische Berichte, vol. 55, 1922, pp. 1112-1138.

Radinov, R.; Haimova, M.; Tadjer A.; Simova, S., "3-Phenylpyrazolo(4,3-c)pyridine and derivatives: structure determination", Journal of Molecular Structure, vol. 158, 1987, pp. 99-108.

Taylor, E. C.; Sobieray, D. M., ""Bicyclobenzodiazepinones" from 3-Oxo-1, 2-diazetidinium Hydroxide, Inner Salts" Tetrahedron, vol. 47, No. 46, 1991, pp. 9599-9620.

Zenchoff, G. S.; Walser, A.; Fryer, R. I., "The Synthesis of Indazoles via 2, 3-Dihydroindazoles (1)", Journal of Heterocyclic Chemistry, vol. 13, 1976, pp. 33-39.

Kuo, Sheng-Chu et al., "Synthesis and Antiplatelets Activity of Ethyl 4(1-benzyl-1*h*-indazol-3-yl)benzoate (YD-3) Analogues", Doctor and Master Thesis, China Medical University, Graduate Institute of Pharmaceutical Chemistry, Taiwan, p. 21, 23 (with English Translation of p.23), Jun. 2002.

* cited by examiner

*Primary Examiner*—Kamal A Saeed
(74) *Attorney, Agent, or Firm*—Howrey LLP; Viola T. Kung

(57) ABSTRACT

Novel compounds of 2-(substituted arylmethyl)-3-(substituted phenyl)-2H-indazoles and 1-(substituted arylmethyl)-3-(substituted phenyl)-1H-indazoles are synthesized, and useful as anti-angiogenic agents.

9 Claims, 9 Drawing Sheets

Scheme 1

Compound 24

| HMBC correlations | |
|---|---|
| $^1$H | $^{13}$C |
| H-4 | C-6, C-7a |
| H-5 | C-3a, C-7 |
| H-6 | C-4, C-7a |
| H-7 | C-3a, C-5 |
| H-2", 6" | -CH$_2$-, C-6", 2", C-4" |
| H-3", 5" | C-1", C-5", 3", C-4"* |
| H-2', 6' | C-3, C-4', C-6', 2' |
| H-3', 5' | 4'-CH$_3$, C-1', C-5', 3' |
| 4"-OCH$_3$ | C-4" |
| 4'-CH$_3$ | C-5", 3', C-4'* |
| N-CH$_2$ | C-2", 6", C-7a |

Compound 25

| HMBC correlations | |
|---|---|
| ¹H | ¹³C |
| H-4 | C-6, C-7a |
| H-5 | C-3a, C-7 |
| H-6 | C-4, C-7a |
| H-7 | C-3a, C-5 |
| H-2", 6" | -CH₂-, C-6", 2", C-4" |
| H-3", 5" | C-1", C-5", 3", C-4"* |
| H-2', 6' | C-3, C-4', C-6', 2' |
| H-3', 5' | 4'-CH₃, C-1', C-5', 3' |
| 4"-OCH₃ | C-4" |
| 4'-CH₃ | C-5", 3', C-4'* |
| N-CH₂ | C-2", 6", C-7a |

Scheme 2

SYNTHESIS OF $N^2$-(SUBSTITUTED ARYLMETHYL)-3-(SUBSTITUTED PHENYL)INDAZOLES AS NOVEL ANTI-ANGIOGENIC AGENTS

CROSS-REFERENCE TO RELATED APPLICATION

This application claims the benefit of U.S. Provisional Application No. 60/628,266, filed 16 Nov. 2004.

FIELD OF THE INVENTION

The present invention is related to novel compounds of 2-(substituted arylmethyl)-3-(substituted phenyl)-2H-indazoles and 1-(substituted arylmethyl)-3-(substituted phenyl)-1H-indazoles are synthesized, which have potential for use as anti-angiogenic agents.

BACKGROUND OF THE INVENTION

In the previous works, we reported that ethyl 4-(1-benzyl-1H-indazol-3-yl)benzoate (YD-3) is a selective and potent inhibitor of protease activated receptor (PAR)-4-dependent activation.[1,2,3] We also discovered that YD-3 effectively inhibits the low thrombin-induced $Ca^{++}$ signal and thromboxane production[4]. Since thrombin and thromboxane play important role in the pathological thrombosis, the ability of YD-3 in selective inhibit thrombin-induced thromboxane production may be of therapeutic benefit for treating thrombotic diseases.

Recently YD-3 and its major metabolite, 4-(1-benzyl-1H-indazol-3-yl)benzoic acid (CHS-6) were found to inhibit vascular endothelial growth factor (VEGF)-induced cell proliferation, migration, and tube formation in human umbilial vein endothelial cells (HUVECs). During in vivo assay, they inhibit VEGF-induced angiogenesis in Matrigel plug animal model.[5] Therefore, these two compounds are considered as very promising candidates for development of novel anti-angiogenic agents.

The previously unknown $N^2$-regioisomer of YD-3 derivatives were synthesized and some of their anti-angiogenic activities were reported in this paper.

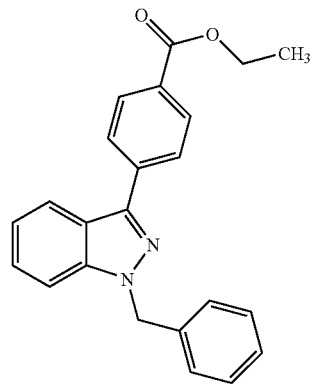

YD-3

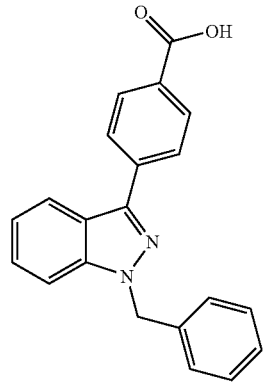

CHS-6

SUMMARY OF THE INVENTION

The present invention synthesizes a novel compound having the following formula:

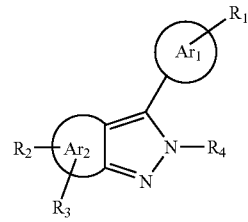

wherein $Ar_1$ is phenyl, pyridinyl or pyrimidinyl;

$Ar_2$ is benzene, pyridine or pyrimidine;

$R_1$ is H, C1-C6 alkyl, carboxyl, C1-C6 alkyloxycarbonyl, halocarbonyl, hydroxyl C1-C6 alkyl,

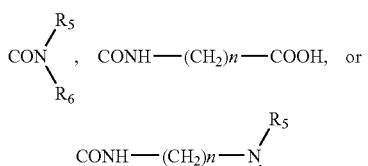

$R_2$ and $R_3$ independently are H, Cl, F, Br, OH, O—R,

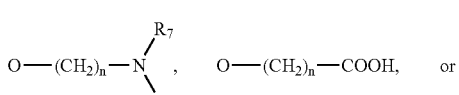

$R_4$ is H, C1-C6 alkyl, $$(CH_2)_n-Ar, \quad \text{or} \quad (CH_2)_n-N\begin{smallmatrix}R_9\\ \\R\end{smallmatrix};$$

wherein $R_5$, $R_6$, $R_7$, $R_8$, $R_9$ and R independently are H, halogen, hydroxyl, or C1-C6 alkyl;

Ar is halogen, C1-C6 alkyl or C1-C6 alkoxyl substituted C6-14 aryl or furyl; and n=1-6.

The present invention also discloses a method for providing anti-angiogenic activities, said method comprising administering to a subject in need of treatment the compound synthesized in the present invention, or a pharmaceutically acceptable salt thereof, in an amount effective to provide anti-angiogenic activities.

The present invention also discloses A method for treating a tumor, said method comprising administering to a subject in need of treatment the compound synthesized in the present invention, or a pharmaceutically acceptable salt thereof, in an amount effective to treat said tumor.

Preferably, $Ar_2$ is benzene.

Preferably, $Ar_1$ is phenyl.

Preferably, $R_4$ is $CH_2$—Ar, wherein Ar is phenyl, halophenyl, methylphenyl or methoxyphenyl.

Preferably, $R_2$ and $R_3$ are hydrogen.

Preferably, $R_1$ is C1-C6 alkyl, carboxyl, C1-C6 alkyloxycarbonyl, hydroxyl C1-C6 alkyl, $$CON\begin{smallmatrix}R_5\\ \\R_6,\end{smallmatrix}$$

wherein $R_5$ and $R_6$ independently are H, hydroxyl, or C1-C6 alkyl. More preferably, $R_1$ is methyl.

DETAILED DESCRIPTION OF THE INVENTION

Figure 1:
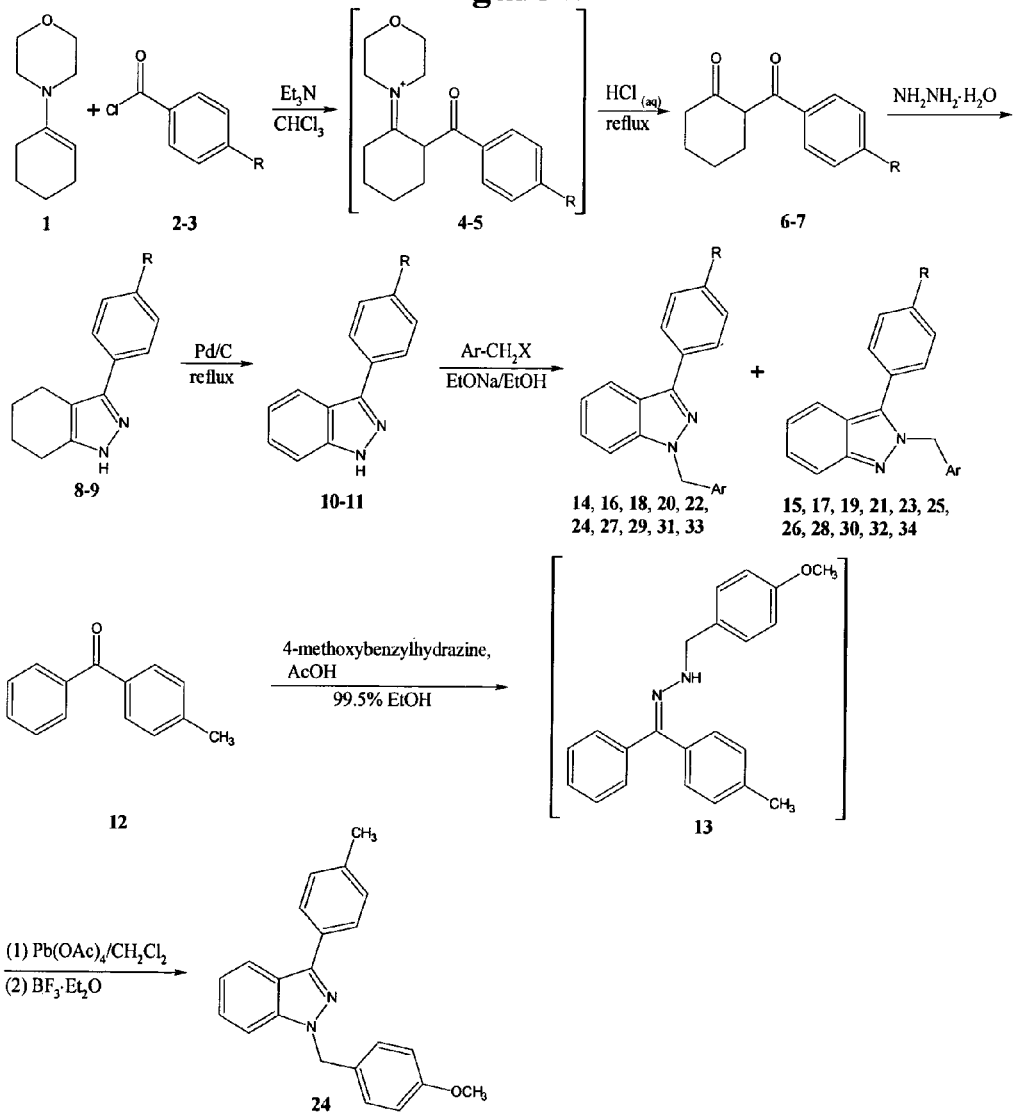
FIG. 1 shows chemical reactions in the synthesis of 2-(substituted arylmethyl)-3-(substituted phenyl)-2H-indazoles and 1-(substituted arylmethyl)-3-(substituted phenyl)-1H-indazoles of the present invention.

In order to search for novel anti-angiogenic compounds, 3-(substituted phenyl)-1H-indazoles (10, 11) were used as the key intermediates and their $N^2$-substituted arylmethyl derivatives (15, 17, 19, 21, 23, 25, 26, 28, 30, 32, 34, 35-40) were synthesized.

In the presence of triethylamine, 1-(N-morpholino)cyclohexene was first treated with substituted arylmethyl chlorides, then hydrolyzed using dil. HCl to yield the corresponding 2-oxo-cyclohexyl substituted phenyl ketones (6, 7) which were subsequently treated with hydrazine hydrate to furnish corresponding 3-(substituted phenyl)-4,5,6,7-tetrahydro-1H-indazoles (8, 9). Then compounds 8 and 9 were oxygenated by catalytic dehydrogenation on Pd/C, to give corresponding 3-(substituted phenyl)-1H-indazoles (10, 11). Alkylation of compounds 10 and 11 with various substituted arymethyl chlorides produced the desired 2-(substituted arylmethyl)-3-(substituted phenyl)-2H-indazoles (15, 17, 19, 21, 23, 25, 26, 28, 30, 32, 34, 35-40) and 1-(substituted arylmethyl)-3-(substituted phenyl)-1H-indazoles (14, 16, 18, 20, 22, 24, 27, 29, 31, 33). The structures of these compounds were identified by their IR, UV, and NMR spectra data.

3-(4-Methylphenyl)-1H-indazole (10) and $N^2$-(substituted benzyl)-3-(4-methylphenyl)indazoles (15, 17, 21, 25, 26) were evaluated for anti-angiogenic activities. Most of $N^2$-substituted benzyl derivatives showed more prominent activity than ethyl 4-(1-benzyl-1H-indazol-3-yl)benzoate (YD-3). Among them, 2-(4-chlorobenzyl)-3-(4-methylphenyl)-2H-indazole (15), 2-(4-methylbenzyl)-3-(4-methylphenyl)-2H-indazole (21) and 2-(4-methoxybenzyl)-3-(4-methylphenyl)-2H-indazole (25) showed significant anti-angiogenic activity and are worthy of further investigation.

The synthesis of $N^2$-(substituted arylmethyl)-3-(substituted phenyl)indazoles (15, 17, 19, 21, 23, 25, 26, 28, 30, 32, 34) was illustrated in Scheme 1, shown in FIG. 1. In the beginning, 1-(N-morpholino)cyclohexene (1) was treated with substituted benzoyl chlorides (2, 3) in the presence of Et₃N to produce the corresponding 4-[2-(substituted benzoyl) cyclohexylidene]morpholin-4-iums (4, 5) which were then acidified with 20% HCl and heated to yield the corresponding 2-oxocyclohexyl substituted phenyl ketones (6, 7). Next, the condensation of compounds 6 and 7 with hydrazine hydrate at room temperature afforded the corresponding 3-(substituted phenyl)-4,5,6,7-tetrahydro-1H-indazoles (8, 9). Subsequent dehydrogenation of compounds 8 and 9 over Pd/C, under elevated temperature, yielded the corresponding key intermediates—3-(substituted phenyl)-1H-indazoles (10, 11). Afterwards, compounds 10 and 11 were subjected to alkylation by treating with various substituted arylmethyl chlorides in EtOH, and in the presence of EtONa to yield the corresponding $N^1$- and $N^2$-regioisomers (14-34). To avoid the redundancy in describing the structural verification procedure for all resulted regioisomers, only the details of structural determination for compound 24 (mp 67-69° C.) and 25 (mp 113-115° C.) were provided in the following as representative examples.

Figure 2:
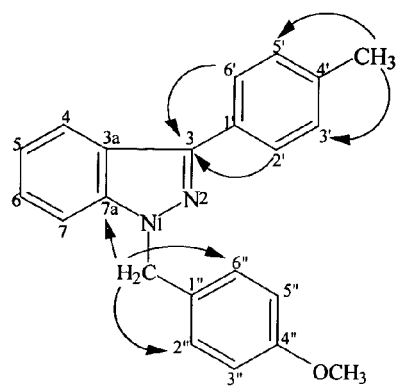
FIG. 2 shows the structure of compound 24 of the present invention and its HMBC spectra.
Figure 3:
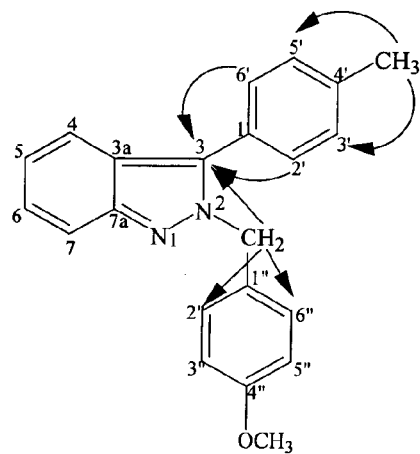
FIG. 3 shows the structure of compound 25 of the present invention and its HMBC spectra.

For both compounds 24 and 25, elemental analysis and mass spectral data [m/z, 328 (M⁺)] established their molecular formula as $C_{22}H_{20}NO$ suggesting that they are possibly the $N^1$- and $N^2$-(p-methoxybenzyl) regioisomers. Although IR, UV, MS and 1D-NMR spectral analysis could not distinguish them, their HMBC spectra were used successfully to confirm their isomeric structures. As shown in FIGS. 2 and 3, the signal of the N—CH₂-moiety of compound 24 showed ³J-correlation with C-7a-, 2"- and 6"-signals. In contrast, the signal of the N—CH₂-moiety of compound 25 exhibited ³J-correlation with its C-3, 2"- and 6"-signals. Based on the above HMBC data, compound 24 (mp 67-69° C. ) was identified as $N^1$-(p-methoxybenzyl)-3-(4-methylphenyl)indazole, and compound 25 (mp 113-115° C.) was confirmed as $N^2$-(p-methoxybenzyl)-3-(4-methylphenyl)indazole. Furthermore, compound 24 could also be obtained by reacting (Z)-(4-methylphenyl)(phenyl)methanone (4-methoxybenzyl)hydrazone (13) with Pb(OAc)₄ and BF₃.Et₂O in $CH_2C_{12}$. The structures for the rest of the N-(substituted arylmethyl) derivatives could be assigned by similar spectral analysis procedures.

After comparing the physical and spectral data of these regioisomers, it was discovered that the melting points of all the $N^1$-regioisomer were relatively lower than their corresponding $N^2$-regioisomer. The similar spectral patterns were observed for the same type of regioisomers. For instance, in the ¹H NMR (DMSO-d₆) spectra of all the $N^1$-regioisomers (14, 16, 18, 20, 22, 24, 27, 29, 31, 33), the signals of four protons appeared in low field correlated well with their H-4, H-2', H-6' and H-7 signals, respectively, in the same order of decreasing chemical shift.

In contrast, it was discovered that both the ¹H NMR and ¹³C NMR spectra of the $N^2$-regioisomers (15, 17, 19, 21, 23, 25, 26, 28, 30, 32, 34) differed slightly from that of their corresponding $N^1$-regioisomers. In the $N^2$-regioisomers, the signals of their four low field protons were assigned to H-7, H-4, H-2' and H-6', respectively, in the order of decreasing chemical shift.

It is worthwhile mentioning that our observations of the difference in mp and NMR spectra between the above regioisomers can be used as valuable reference when dealing with structure verification of related regioisomers.

Figure 4:
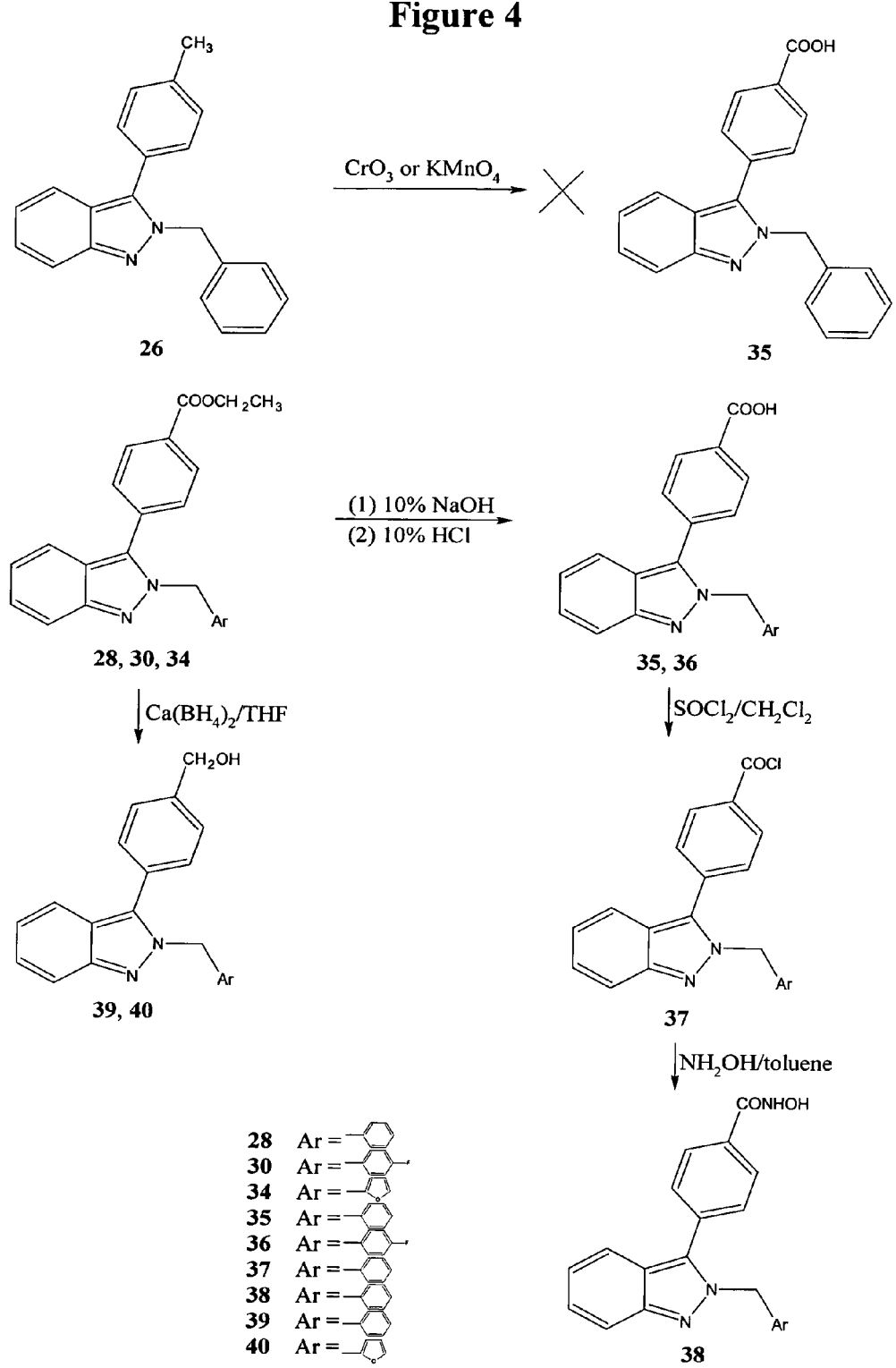
FIG. 4 shows chemical reactions in the synthesis of compounds 35-40 of the present invention.

As shown in Scheme 2, shown in FIG. 4, when ethyl 4-[1-(substituted benzyl)-1H-indazol-3-yl]benzoate (28, 30) were hydrolyzed with 10% NaOH, the corresponding acids (35, 36) were obtained in good yield. Compound 36 was allowed to react with SOCl₂ to afford acid chloride (37), which was treated with hydroxyamine to give amides (38).

Our attempt to prepare compound 35 from compound 26, by treating compound 26 with a variety of oxidizing agents like CrO₃ or KMnO₄, however, did not afford the desired compound (35), but resulted in a mixture of compounds that were not easily separable.

Experimental

All of the solvents and reagents were obtained commercially and used without further purification. Reactions were monitored by thin-layer chromatography, using Merck plates with fluorescent indicator. Column chromatography was performed on silica gel.

Melting points were determined on a Yanaco MP-500D melting point apparatus and are uncorrected. IR spectra were recorded on Shimadzu IR-440 and Nicolet Impact 400 FT-IR spectrophotometers as KBr pellets. NMR spectra were obtained on a Bruker Avance DPX-200 FT-NMR spectrometer in CDCl₃ and DMSO-d₆. The following abbreviations are used: s, singlet; d, doublet; dd, double doublet; t, triplet; q, quartet; m, multiplet; and br, broad. MS spectra were measured with an HP 5995 GC-MS instrument. The UV spectra were recorded on a Shimadzu UV-160A UV-Vis recording spectrophotometer as methanolic solutions. Elemental analyses (C, H, N) were performed on a Perkin-Elmer 2400 Series II CHNS/O analyzer and the results were within ±0.4% of the calculated values.

3-(4-Methylphenyl)-1H-indazole (10)

(A). Into a solution of 1-(N-morpholino)cyclohexene (1) (33.4 g, 0.2 mol) and triethylamine (28 mL) in CHCl₃ (100 mL) was added dropwise the solution of 4-methylbenzoyl chloride (2) (26.42 ml, 0.2 mol) in CHCl₃ (40 mL) at 45° C. The reaction mixture was allowed to react for 3 h. Then 20% HCl was added, and the mixture was heated under reflux for 5 h and then standed to room temperature. The CHCl₃ layer was collected and washed with H₂O and dried over MgSO₄ and then evaporated. The residue was washed with petroleum ether, and dried to yield 2-oxycyclohexyl-4-methylphenyl ketone (6, 21.2 g, 49%).

(B) Compound 6 (13.01 g, 0.06 mol) was dissolved in MeOH (100 mL), then 4 ml of 85% NH₂NH₂.H₂O was added dropwise at 30±2° C. The mixture was allowed to react for 30 min, and was then concentrated in vacuo until there are about 35 mL solution left. The residue was allowed to precipitate during cooling. The solid precipitate was washed with petroleum ether, and dried to yield 3-(4-methylphenyl)-4,5,6,7-tetrahydro-1H-indazole (8, 12.39 g, 97% yield), mp 57.4-59.9° C.

(C) Into the solution of compound 8 (12.3 g, 0.058 mol) in trans-decahydronaphthalene (trans-decalin) was added 10% Pd/C (2.7 g), and the mixture was heated under reflux for 4 h, and then concentrated in vacuo in oil bath until there were about 20 mL solution left. Petroleum ether (80 mL) was added into the residue while hot, and the mixture was well mixed by shaking. The mixture was allowed to precipitate upon cooling to afford 3-(4-methylphenyl)-1H-indazole (10, 9.85 g, 82% yield).

mp 106-107° C.; MS (EI, 70 eV): m/z 208 (M⁺); UV, $\lambda_{max}$ (CHCl₃) nm (log ε): 233.4 (3.850), 246.0 (4.223), 311.6 (4.251); ¹H NMR (200 MHz, CDCl₃): δ 2.47 (3H, s, 4'-CH₃), 7.19-7.29 (2H, m, H-5, H-7), 7.34-7.38 (3H, m, H-6, H-3', 5'), 7.93 (2H, d, J=8.0 Hz, H-2', 6'), 8.03 (1H, d, J=8.1 Hz, H-4); ¹³C NMR (50 MHz, CDCl₃): ε 21.33 (4'-CH₃), 110.26 (C-7), 120.92 (C-3a), 121.17 (C-4 C-5), 126.70 (C-6), 127.60 (C-2', 6'), 129.62 (C-3', 5'), 130.65(C-1'), 138.02 (C-4'), 141.66

(C-7a), 145.68 (C-3). Anal. Calcd. for $C_{14}H_{12}N_2$: C, 80.74; H, 5.81; N, 13.45. Found: C, 80.70; H, 5.75; N, 13.40.

Ethyl 4-(1H-indazol-3-yl)benzoate (11)

Ethyl 4-(chlorocarbonyl)benzoate was treated as in the preparation of 10 to afford 11 (0.94 g, 88.9%).

mp 133-135° C.; MS (EI, 70 eV): m/z 266 (M$^+$); $^1$H NMR (200 MHz, DMSO-$d_6$): δ 1.33 (3H, t, J=7.0 Hz, $CH_3$), 4.32 (2H, q, J=7.0 Hz, $OCH_2$), 7.20-7.27 (1H, m, H-5), 7.38-7.45 (1H, m, H-6), 7.62 (1H, d, J=8.4 Hz, H-7), 8.08 (2H, d, J=8.4 Hz, H-3', 5'), 8.12 (1H, d, J=9.2 Hz, H-4), 8.16 (2H, d, J=8.4 Hz, H-2', 6'), 13.47 (1H, s, NH). Anal. Calcd. for $C_{16}H_{14}N_2O_2$: C, 72.16; H, 5.30; N, 10.52. Found: C, 72.18; H, 5.29; N, 10.52.

1-(4-Chlorobenzyl)-3-(4-methylphenyl)-1H-indazole (14) and 2-(4-Chlorobenzyl)-3-(4-methylphenyl)-2H-indazole (15)

Into the solution of compound 10 (4.16 g, 0.02 mol) in anhydrous EtOH (30 mL) was added EtONa (2.72 g, 0.04 mol). The mixture was stirred at 30±2° C. for 1.5 h. 4-Chlorobenzyl chloride (6.44 g, 0.04 mol) was added dropwise, and mixture was heated under reflux for 1.5 h. The solid precipitate so formed was filter off while hot and washed several times with $CHCl_3$. The combined filtrate was concentrated in vacuo for solvent removal. The residue was chromatographed (silica gel-$CHCl_3$) to produce compound 14 (3.1 g, 47%) and compound 15 (0.23 g, 3%).

Compound 14: mp: 79.9-82.3° C.; MS (EI, 70 eV): m/z 332 (M$^+$); UV, $\lambda_{max}$ ($CHCl_3$) nm (log ε): 232.2 (3.769), 244.6 (4.079), 313.4 (4.099); $^1$NMR (200 MHz, $CDCl_3$): δ 2.35 (3H, s, 4'-$CH_3$), 5.52 (2H, s, $CH_2$), 7.06-7.28 (9H, m, aromatic H), 7.79 (2H, d, J=8.1 Hz, H-2', 6'); $^{13}$C NMR (50 MHz, $CDCl_3$): δ 21.33 (4'-$CH_3$), 52.26 ($CH_2$), 109.34 (C-7), 121.08 (C-4), 121.59 (C-5), 122.13 (C-3a), 126.48 (C-6), 127.38, 128.48, 128.85, 129.52, 130.61 (C-1'), 133.52 (C-4"), 135.42 (C-1"), 137.82 (C-4'), 140.95 (C-7a), 144.52 (C-3). Anal. Calcd. for $C_{21}H_{17}N_2$: C, 75.78; H, 5.15; N, 8.42. Found: C, 75.74; H, 5.13; N, 8.41.

Compound 15: mp: 107.4-109.5° C.; MS (EI, 70 eV): m/z 332 (M$^+$); UV, $\lambda_{max}$ ($CHCl_3$) nm (log ε): 232.4 (3.683), 244.8 (3.996), 314.6 (4.056); $^1$H NMR (200 MHz, $CDCl_3$): δ 2.45 (3H, s, 4'-$CH_3$), 5.59 (2H, s, $CH_2$), 7.01-7.32 (10H, m, aromatic H), 7.57 (1H, d, J=8.4 Hz, H-4), 7.74 (1H, d, J=8.7 Hz, H-7); $^{13}$C NMR (50 MHz, $CDCl_3$): δ 21.17 (4'-$CH_3$), 53.38 ($CH_2$), 117.13 (C-7), 120.23 (C-4), 121.09 (C-3a), 121.68 (C-5), 126.25 (C-1'), 126.35 (C-6), 128.14, 128.63, 129.30, 129.57, 133.38 (C-4"), 135.22 (C-1"), 136.48 (C-3), 138.89 (C-4'), 148.15 (C-7a). Anal. Calcd. for $C_{21}H_{17}N_2$: C, 75.78; H, 5.15; N, 8.42. Found: C, 75.69; H, 5.10; N, 8.38.

1-(3-Chlorobenzyl)-3-(4-methylphenyl)-1H-indazole (16) and 2-(3-Chlorobenzyl)-3-(4-methylphenyl)-2H-indazole (17)

Compound 10 (10.4 g, 0.05 mol), EtONa (6.8 g, 0.1 mol) and 3-chlorobenzyl chloride (16.1 g, 0.1 mol) were allowed to reacted as in the preparation of compounds 14 and 15 to afford compound 16 (7.1 g, 43%) and compound 17 (0.76 g, 5%).

Compound 16: mp: 66.6-68° C.; MS (EI, 70 eV): m/z 332 (M$^+$); UV, $\lambda_{max}$ ($CHCl_3$) nm (log ε): 233.2 (3.797), 245.4 (4.09), 313.0 (4.107); $^1$NMR (200 MHz, $CDCl_3$): δ 2.32 (3H, s, 4'-$CH_3$), 5.48 (2H, s, $CH_2$), 6.98-6.99 (1H, m, H-4"), 7.05-7.25 (8H, m, aromatic H), 7.78 (2H, d, J=8.1 Hz, H-2', 6'), 7.92 (1H, d, J=8.1 Hz, H-4); $^{13}$C NMR (50 MHz, $CDCl_3$): δ 21.30 (4'-$CH_3$), 52.24 ($CH_2$), 109.27 (C-7), 121.09 (C-4), 121.56 (C-5), 122.09 (C-3a), 125.20 (C-4"), 126.50 (C-6), 127.18 (C-6"), 127.37 (C-2', 6'), 127.87 (C-2"), 129.49 (C-3', 5'), 129.95 (C-5"), 130.57 (C-1'), 134.53 (C-3"), 137.80 (C-4'), 138.93 (C-1"), 140.97 (C-7a), 144.56 (C-3). Anal. Calcd. for $C_{21}H_{17}N_2$: C, 75.78; H, 5.15; N, 8.42. Found: C, 75.68; H, 5.09; N, 8.39.

Compound 17: mp: 98-100° C.; MS (EI, 70 eV): m/z 332 (M$^+$); UV, $\lambda_{max}$ ($CHCl_3$) nm (log ε): 232.2 (3.706), 244.2 (4.007), 313.4 (4.047); $^1$NMR (200 MHz, $CDCl_3$): δ 2.37 (3H, s, 4'-$CH_3$), 5.51 (2H, s, $CH_2$), 6.86-7.29 (10H, m, aromatic H), 7.50 (1H, dd, J=1.0, 8.4 Hz, H-4), 7.67 (1H, dd, J=0.9, 8.7 Hz, H-7); $^{13}$C NMR (50 MHz, $CDCl_3$): δ 21.36 (4'-$CH_3$), 53.64 ($CH_2$), 117.36 (C-7), 120.44 (C-4), 121.26 (C-3a), 121.91 (C-5), 125.08 (C-4"), 126.39 (C-1'), 126.58 (C-6), 127.10 (C-6"), 127.95 (C-5"), 129.51 (C-2', 6'), 129.78 (C-3', 5'), 129.96 (C-2"), 134.59 (C-3"), 136.79 (C-3), 138.84 (C-4'), 139.13 (C-1"), 148.37 (C-7a). Anal. Calcd. for $C_{21}H_{17}N_2$: C, 75.78; H, 5.15; N, 8.42. Found: C, 75.72; H, 5.13; N, 8.41.

1-(2-Chlorobenzyl)-3-(4-methylphenyl)-1H-indazole (18) and 2-(2-Chlorobenzyl)-3-(4-methylphenyl)-2H-indazole (19)

Compound 10 (10.4 g, 0.05 mol), EtONa (6.8 g, 0.1 mol) and 2-chlorobenzyl chloride (16.1 g, 0.1 mol) were allowed to reacted as in the preparation of compounds 14 and 15 to afford compound 18 (7.3 g, 44%) and compound 19 (0.58 g, 3%).

Compound 18: mp: 77.6-78.8° C.; MS (EI, 70 eV): m/z 332 (M$^+$); UV, $\lambda_{max}$ ($CHCl_3$) nm (log ε): 232.4 (3.659), 245.4 (3.94), 312.6 (3.995); $^1$NMR (200 MHz, $CDCl_3$): δ 2.35 (3H, s, 4'-$CH_3$), 5.69 (2H, s, $CH_2$), 6.70-7.35 (9H, m, aromatic H), 7.81 (2H, d, J=8.1 Hz, H-2', 6'), 7.96 (1H, d, J=8.1 Hz, H-4); $^{13}$C NMR (50 MHz, $CDCl_3$): δ 21.30 (4'-$CH_3$), 50.00 ($CH_2$), 109.44 (C-7), 121.12 (C-4), 121.50 (C-5), 121.94 (C-3a), 126.52 (C-6), 127.10 (C-5"), 127.37 (C-2', 6'), 128.31 (C-3"), 128.75 (C-4"), 129.34 (C-6"), 129.49 (C-3', 5'), 130.66 (C-1'), 132.24 (C-2"), 134.67 (C-1"), 137.79 (C-4'), 141.32 (C-7a), 144.69 (C-3). Anal. Calcd. for $C_{21}H_{17}N_2$: C, 75.78; H, 5.15; N, 8.42. Found: C, 75.57; H, 4.79; N, 8.49.

Compound 19: mp: 131.3-137.8° C.; MS (EI, 70 eV): m/z 332 (M$^+$); UV, $\lambda_{max}$ ($CHCl_3$) nm (log ε): 232.8 (3.691), 244.6 (4.007), 314.8 (4.06); $^1$NMR (200 MHz, $CDCl_3$): ε 2.43 (3H, s, 4'-$CH_3$), 5.74 (2H, s, $CH_2$), 6.63-7.40 (10H, m, aromatic H), 7.64 (1H, d, J=8.5 Hz, H-4), 7.76 (1H, d, J=8.7 Hz, H-7); $^{13}$C NMR (50 MHz, $CDCl_3$): δ 21.33 (4'-$CH_3$), 51.95 ($CH_2$), 117.43 (C-7), 120.55 (C-4), 121.12 (C-3a), 121.94 (C-5), 126.33 (C-1'), 126.57 (C-6), 127.28 (C-5"), 127.84 (C-3"), 128.78 (C-4"), 129.19 (C-2', 6'), 129.20 (C-6"), 129.80 (C-3', 5'), 131.73 (C-2"), 135.04 (C-1"), 137.23 (C-3), 139.01 (C-4'), 148.56 (C-7a). Anal. Calcd. for $C_{21}H_{17}N_2$: C, 75.78; H, 5.15; N, 8.42. Found: C, 75.74; H, 5.10; N, 8.38.

1-(4-Methylbenzyl)-3-(4-methylphenyl)-1H-indazole (20) and 2-(4-Methylbenzyl)-3-(4-methylphenyl)-2H-indazole (21)

Compound 10 (4.16 g, 0.02 mol), EtONa (2.72 g, 0.04 mol) and 4-methylbenzyl chloride (6.33 g, 0.045 mol) were allowed to reacted as in the preparation of compounds 14 and 15 to afford compound 20 (3.1 g, 50%) and compound 21 (0.4 g, 6%).

Compound 20: mp: 79.6-82.3° C.; MS (EI, 70 eV): m/z 312 (M$^+$); UV, $\lambda_{max}$ ($CHCl_3$) nm (log ε): 232.8 (3.806), 243.4

(4.090), 313.8 (4.096); $^1$H NMR (200 MHz, CDCl$_3$): δ 2.21 (3H, s), 2.34 (3H, s), 5.53 (2H, s, CH$_2$), 6.99-7.26 (9H, m, aromatic H), 7.80 (2H, d, J=8.1 Hz, H-2', 6'), 7.92 (1H, d, J=8.1 Hz, H-4); $^{13}$C NMR (50 MHz, CDCl$_3$): δ 21.07, 21.31, 52.85 (CH$_2$), 109.62 (C-7), 120.86 (C-4), 121.44 (C-5), 122.10 (C-3a), 126.22 (C-6), 127.14, 127.38, 129.32, 129.46, 130.83 (C-1'), 133.90 (C-1"), 137.34 (C-4"), 137.62 (C-4'), 140.95 (C-7a), 144.10 (C-3). Anal. Calcd. for C$_{22}$H$_{20}$N$_2$: C, 84.58; H, 6.45; N, 8.97. Found: C, 84.55; H, 6.41; N, 8.93.

Compound 21: mp: 107.5-109.3° C.; MS (EI, 70 eV): m/z 312 (M$^+$); UV, λ$_{max}$ (CHCl$_3$) nm (log ε): 33.8 (3.723), 243 (4.046), 266.0 (3.883), 314.6(4.06); $^1$H NMR (200 MHz, CDCl$_3$): δ 2.31 (3H, s), 2.45 (3H, s), 5.60 (2H, s, CH$_2$), 6.98-7.39 (10H, m, aromatic H), 7.48 (1H, dd, J=1.0, 8.4 Hz,H-4),7.66 (1H, dd, J=0.9, 8.7 Hz, H-7); $^{13}$C NMR (50 MHz, CDCl$_3$): δ 21.06, 21.34, 54.03 (CH$_2$), 117.39 (C-7), 120.40 (C-4), 121.28 (C-3a), 121.62 (C-5), 126.23 (C-6), 126.73 (C-1'), 126.90, 129.30, 129.62, 133.98 (C-1"), 136.49 (C-3), 137.32 (C-4"), 138.83 (C-4'), 148.29 (C-7a). Anal. Calcd. for C$_{22}$H$_{20}$N$_2$: C, 84.58; H, 6.45; N, 8.97. Found: C, 84.48; H, 6.39; N, 8.88.

1-(2-Methylbenzyl)-3-(4-methylphenyl)-1H-indazole (22) and 2-(2-Methylbenzyl)-3-(4-methylphenyl)-2H-indazole (23)

Compound 10 (4.16 g, 0.02 mol), EtONa (2.72 g, 0.04 mol) and 2-methylbenzyl chloride (6.33 g, 0.045 mol) were allowed to reacted as in the preparation of compounds 14 and 15 to afford compound 22 (3.05 g, 49%) and compound 23 (0.28 g, 4%).

Compound 22: mp: 114.1-116.5° C.; MS (EI, 70 eV): m/z 312 (M$^+$); UV, λ$_{max}$(CHCl$_3$) nm (log ε): 33.2 (3.814), 244.8 (4.092), 314.2 (4.128); $^1$NMR (200 MHz, CDCl$_3$): δ 2.33 (3H, s), 2.34 (3H, s), 5.57 (2H, s, CH$_2$), 6.72-6.75 (1H, d, aromatic H), 6.97-7.25 (9H, m, aromatic H), 7.80 (2H, dd, J=1.8, 8.2 Hz, H-2', 6'), 7.95 (1H, dd, J=1.0, 8.1 Hz, H-4); $^{13}$C NMR (50 MHz, CDCl$_3$): δ 19.35, 21.31, 51.27 (CH$_2$), 109.61 (C-7), 120.92 (C-4), 121.49 (C-5), 121.96 (C-3a), 126.20 (C-4"), 126.28 (C-6), 127.30 (C-5"), 127.36 (C-2', 6'), 127.63 (C-3"), 129.47 (C-3', 5'), 130.42 (C-6"), 130.78 (C-1'), 134.90 (C-2"), 135.70 (C-1"), 137.67 (C-4'), 141.28 (C-7a), 144.14 (C-3). Anal. Calcd. for C$_{22}$H$_{20}$N$_2$: C, 84.58; H, 6.45; N, 8.97. Found: C, 84.57; H, 6.41; N, 8.95.

Compound 23: mp: 125-128.8° C.; MS (EI, 70 eV): m/z 312 (M$^+$); UV, λ$_{max}$(CHCl$_3$) nm (log ε): 232.6 (3.695), 243.4 (3.995), 315.2 (4.102); $^1$NMR (200 MHz, CDCl$_3$): δ 2.16 (3H, s), 2.35 (3H, s), 5.54 (2H, s, CH$_2$), 6.52-6.55 (1H, d, aromatic H), 6.98-7.30 (9H, m, aromatic H), 7.55 (1H, d, J=8.4 Hz, H-4), 7.67 (1H, d, J=8.7 Hz, H-7); $^{13}$C NMR (50 MHz, CDCl$_3$): δ 19.07, 21.33, 52.21 (CH$_2$), 117.46 (C-7), 120.45 (C-4), 121.14 (C-3a), 121.73 (C-5), 126.30 (C-4"), 126.44 (C-6, 5"), 126.67 (C-1'), 127.46 (C-3"), 129.27 (C-2', 6'), 129.71 (C-3', 5'), 130.10 (C-6"), 134.54 (C-2"), 135.46 (C-1"), 126.84 (C-3), 138.85 (C-4'), 148.41 (C-7a). Anal. Calcd. for C$_{22}$H$_{20}$N$_2$: C, 84.58; H, 6.45; N, 8.97. Found: C, 84.49; H, 6.41; N, 8.91.

1-(4-Methoxylbenzyl)-3-(4-methylphenyl)-1H-indazole (24) and 2-(4-Methoxylbenzyl)-3-(4-methylphenyl)-2H-indazole (25)

Compound 10 (10.4 g, 0.05 mol), EtONa (6.8 g, 0.1 mol) and 4-methoxylbenzyl chloride (23.5 g, 0.15 mol) were allowed to reacted as in the preparation of compounds 14 and 15 to afford compound 24 (7.3 g, 46%) and compound 25 (0.49 g, 3%).

Method A: Compound 24: mp: 66.3-69.1° C.; MS (EI, 70 eV): m/z 328 (M$^+$); UV, λ$_{max}$(CHCl$_3$) nm (log ε): 232.8 (4.801), 243.4 (4.107), 313.8 (4.091); $^1$H NMR (200 MHz, CDCl$_3$): δ 2.31 (3H, s, 4'-CH$_3$), 3.63 (3H, s, 4"-OCH$_3$), 5.59 (2H, s, CH$_2$), 6.81 (2H, d, J=8.6 Hz, H-3", 5"), 7.18 (1H, dd, J=7.5, 7.5 Hz, H-5), 7.24 (2H, d, J=8.6 Hz, H-2", 6"), 7.28 (2H, d, J=8.0 Hz, H-3', 5'), 7.38 (1H, dd, J=7.6, 7.6 Hz, H-6), 7.68 (1H, d, J=8.6 Hz, H-7), 7.87 (2H, d, J=8.0 Hz, H-2', 6'), 8.00 (1H, d, J=8.2 Hz, H-4); $^{13}$C NMR (50 MHz, CDCl$_3$): δ 21.12 (4'-CH$_3$), 51.76 (CH$_2$), 55.26 (4"-OCH$_3$), 110.53 (C-7), 114.20 (C-3", 5"), 121.28 (C-3a), 121.35 (C-4), 121.51 (C-5), 126.61 (C-6), 127.08 (C-2', 6'), 129.16 (C-2", 6"), 129.60 (C-1"), 129.80 (C-3', 5'), 130.82 (C-1'), 137.51 (C-4'), 140.98 (C-7a), 143.02 (C-3), 159.02 (C-4"). Anal. Calcd. for C$_{22}$H$_{20}$N$_2$: C, 80.46; H, 6.14; N, 8.53. Found: C, 80.43; H, 6.11; N, 8.50.

Compound 25: mp: 113.6-115° C.; MS (EI, 70 eV): m/z 328 (M$^+$); UV, λ$_{max}$(CHCl$_3$) nm (log ε): 232.8 (3.769), 243.0 (4.083), 313.8 (4.065); $^1$NMR (200 MHz, CDCl$_3$): δ 2.37 (3H, s, 4'-CH$_3$), 3.66 (3H, s, 4"-OCH$_3$), 5.50 (2H, s, CH$_2$), 6.80 (2H, d, J=8.7 Hz, H-3", 5"), 6.97 (2H, d, J=8.7 Hz, H-2", 6"), 7.03 (1H, dd, J=7.5, 7.5 Hz, H-5), 7.26 (1H, dd, J=8.0, 8.0 Hz, H-6), 7.35 (2H, d, J=8.1 Hz, H-3', 5'), 7.40 (2H, d, J=8.2 Hz, H-2', 6'), 7.49 (1H, d, J=8.5 Hz, H-4), 7.62 (1H, d, J=8.7 Hz, H-7); $^{13}$C NMR (50 MHz, CDCl$_3$): δ 21.15 (4'-CH$_3$), 53.47 (CH$_2$), 55.27 (4"-OCH$_3$), 114.13 (C-3",5"), 117.28 (C-7), 120.41 (C-4), 120.96 (C-3a), 121.85 (C-5), 126.28 (C-6), 126.41 (C-1'), 128.65 (C-2", 6"), 129.26 (C-1"), 129.57 (C-2', 6'), 130.05 (C-3', 5'), 135.69 (C-3), 138.74 (C-4'), 147.70 (C-7a), 158.87 (C-4"). Anal. Calcd. for C$_{22}$H$_{20}$N$_2$: C, 80.46; H, 6.14; N, 8.53. Found: C, 80.42; H, 6.13; N, 8.51.

Method B: To a solution of (4-methylphenyl)(phenyl)methanone (12) (1.9 g, 0.01 mol) in methanol was added 4-methoxybenzyl hydrazine (4.5 g, 0.035 mol) and acetic acid (0.5 mL). The mixture was reflux for 2 h. After cooling, the mixture was concentrated and the residue was extracted with CHCl$_3$, washed with dil. HCl, followed by water, dried over MgSO$_4$ and concentrated in vacuo, to give (Z)-(4-methylphenyl)(phenyl)methanone (4-methoxybenzyl)hydrazone (13). Next, a solution of above benzylhydrazone was dissolved in CH$_2$Cl$_2$ (50 ml) was added dropwise to a solution of Pb(OAC)$_4$ (14.1 g, 0.03 mol) in CH$_2$Cl$_2$ (200 mL). After addition was completed, the mixture was reacted at 30±2° C. for 30 min, the BF$_3$.Et$_2$O (containing 47% of BF$_3$ 61 mL) was added. The mixture was reflux for 30 min before quenched into ice water. The organic layer was washed with water, dried over MgSO$_4$ and evaporated. The residue was purified by column chromatography (silica gel-toluene) produce compound 24 (0.6 g). This product was confirmed by comparison of its IR and NMR spectra with that of a sample from the method A.

2-Benzyl-3-(4-methylphenyl)-2H-indazole (26)

Compound 10 (6.24 g, 0.03 mol), EtONa (4.08 g, 0.06 mol) and benzyl chloride (10.18 g, 0.08 mol) were allowed to react as in the preparation of compound 15 to afford compound 26 (0.45 g, 5%).

Compound 26: mp: 110.7-111.3° C.; MS (EI, 70 eV): m/z 298 (M$^+$); UV, λ$_{max}$ (CHCl$_3$) nm (log ε): 233.2 (3.641), 243 (3.956), 314.6 (3.972); $^1$H NMR (200 MHz, CDCl$_3$): δ 2.37 (3H, s, 4'-CH$_3$), 5.50 (2H, s, CH$_2$), 6.92-7.23 (10H, m, aromatic H), 7.48 (1H, d, J=8.4 Hz, H-4), 7.66 (1H, d, J=8.7 Hz, H-7); $^{13}$C NMR (50 MHz, CDCl$_3$): δ 21.36 (4'-CH$_3$), 53.56 (CH$_2$), 117.31 (C-7), 120.42 (C-4), 121.27 (C-3a), 121.86 (C-5), 126.43 (C-1'), 126.53 (C-6), 128.32, 128.82, 129.49, 129.75, 133.56 (C-1"), 135.41 (C-4"), 136.67 (C-3), 139.07 (C-4'), 148.34 (C-7a). Anal. Calcd. for $C_{20}H_{18}N_2$: C, 80.46; H, 6.14; N, 8.53. Found: C, 84.50; H, 6.02; N, 9.34.

Ethyl 4-(1-benzyl-1H-indazol-3-yl)benzoate (27) and Ethyl 4-(2-benzyl-2H-indazol-3-yl)benzoate (28)

Compound 11 (4.26 g, 0.016 mol), EtONa (3.54 g, 0.052 mol) and benzyl chloride (20.36 g, 0.16 mol) were allowed to react as in the preparation of compounds 14 and 15 to afford compound 27 (3.09 g, 54.3%) and compound 28 (0.50 g, 8.8%).

Compound 27: mp: 79-81° C.; MS (EI, 70 eV): m/z 356 ($M^+$); UV; $\lambda_{max}$ (MeOH) nm (log $\epsilon$): 320 (4.6), 211 (4.7); $^1$H NMR (200 MHz, DMSO-$d_6$): δ 1.32 (3H, t, J=7.1 Hz, $CH_3$), 4.33 (2H, q, J=7.1 Hz, $OCH_2$), 5.75 (2H, s, $CH_2$), 7.22-7.30 (6H, m, H-5, 2", 3", 4", 5", 6"), 7.44 (1H, t, J=7.0 Hz, H-6), 7.78 (1H, d, J=8.5 Hz, H-7), 8.06-8.10 (2H, m, H-3', 5'), 8.12 (1H, d, J=7.5 Hz, H-4), 8.15-8.18 (2H, m, H-2', 6'). Anal. Calcd. for $C_{23}H_{20}N_2$: C, 77.51; H, 6.14; N, 5.66. Found: C, 77.48; H, 5.68; N, 7.88.

Compound 28: mp: 112-113° C.; MS (EI, 70 eV): m/z 356 ($M^+$); $^1$H NMR (200 MHz, DMSO-$d_6$): δ 1.31 (3H, t, J=7.1 Hz, $CH_3$), 4.33 (2H, q, J=7.1 Hz, $OCH_2$), 5.70 (2H, s, $CH_2$), 6.98-7.04 (2H, m, H-2", 6"), 7.09-7.14 (1H, m, H-5), 7.19-7.24 (3H, m, H-3", 4", 5"), 7.27-7.34 (1H, m, H-6), 7.56 (1H, d, J=8.4 Hz, H-4), 7.69 (3H, d, J=8.3 Hz, H-7, 2', 6'), 8.09 (2H, d, J=8.3 Hz, H-3', 5'). Anal. Calcd. for $C_{23}H_{20}N_2$: C, 77.51; H, 6.14; N, 5.66. Found: C, 77.49; H, 5.65; N, 7.87.

Methyl 4-[1-(4-fluorobenzyl)-1H-indazol-3-yl]benzoate (29) and Methyl 4-[2-(4-fluorobenzyl)-2H-indazol-3-yl]benzoate (30)

Compound 11 (4.26 g, 0.016 mol), MeONa (2.81 g, 0.052 mol) and 4-fluorobenzyl chloride (23.1 mL, 0.16 mol) were allowed to react as in the preparation of compounds 14 and 15 to afford compound 29 (3.35 g, 58.2%) and compound 30 (0.58 g, 10.1%).

Compound 29: mp: 118-120° C.; MS (EI, 70 eV): m/z 360 ($M^+$); $^1$NMR (200 MHz, DMSO-$d_6$): δ3.87 (3H, s, $CH_3$), 5.74 (2H, s, $CH_2$), 7.09-7.18 (2H, m, H-3", 5"), 7.27-7.32 (3H, m, H-5, 2", 6"), 7.35-7.391 (1H, m, H-6), 7.82 (1H, d, J=8.5 Hz, H-7), 8.06-8.18 (5H, m, H-4, 2', 3', 5', 6'). Anal. Calcd. for $C_{22}H_{17}N_2$: C, 73.32; H, 4.75; N, 7.77. Found: C, 73.31; H, 4.74; N, 7.78.

Compound 30: mp: 121-122° C.; MS (EI, 70 eV): m/z 360 ($M^+$); $^1$H NMR (200 MHz, DMSO-$d_6$): δ3.89 (3H, s, $CH_3$), 5.70 (2H, s, $CH_2$), 7.06-7.15 (5H, m, H-5, 2", 3", 5", 6"), 7.28-7.36 (1H, m, H-6), 7.57 (1H, d, J=8.4 Hz, H-4), 7.67-7.73 (3H, m, H-7, 2', 6'), 8.12 (2H, d, J=8.3 Hz, H-3', 5'). Anal. Calcd. for $C_{22}H_{17}N_2$: C, 73.32; H, 4.75; N, 7.77. Found: C, 73.29; H, 4.74; N, 7.79.

Ethyl 4-[1-(2-fluorobenzyl)-1H-indazol-3-yl]benzoate (31) and Ethyl 4-[2-(2-fluorobenzyl)-2H-indazol-3-yl]benzoate (32)

Compound 11 (4.26 g, 0.016 mol), EtONa (3.54 g, 0.052 mol) and 2-fluorobenzyl chloride (23.1 mL, 0.16 mol) were allowed to react as in the preparation of compounds 14 and 15 to afford compound 31 (3.40 g, 56.9%) and compound 32 (0.38 g, 6.4%).

Compound 31: mp: 102-103° C.; MS (EI, 70 eV): m/z 374 ($M^+$); $^1$H NMR (200 MHz, DMSO-$d_6$): δ 1.33 (3H, t, J=7.1 Hz, $CH_3$), 4.33 (2H, q, J=7.1 Hz, $OCH_2$), 5.80 (2H, s, $CH_2$), 7.11-7.32 (5H, m, H-5, 3", 4", 5", 6"), 7.44-7.52 (1H, m, H-6), 7.80 (1H, d, J=8.5 Hz, H-7), 8.05-8.16 (5H, m, H-4, 2', 3', 5', 6'). Anal. Calcd. for $C_{23}H_{19}N_2$: C, 73.78; H, 5.11; N, 7.48. Found: C, 73.76; H, 5.09; N, 7.49.

Compound 32: mp: 94-96° C.; MS (EI, 70 eV): m/z 374 ($M^+$); $^1$H NMR (200 MHz, DMSO-$d_6$): δ 1.34 (3H, t, J=7.1 Hz, $CH_3$), 4.35 (2H, q, J=7.1 Hz, $OCH_2$), 5.74 (2H, s, $CH_2$), 7.00-7.17 (4H, m, H-5, 3", 4", 5"), 7.27-7.35 (2H, m, H-6, 6"), 7.57 (1H, d, J=8.4 Hz, H-4), 7.66 (1H, d, J=8.7 Hz, H-7), 7.76 (2H, d, J=8.3 Hz, H-2', 6'), 8.13 (2H, d, J=8.3 Hz, H-3', 5'). Anal. Calcd. for $C_{23}H_{19}N_2$: C, 73.78; H, 5.11; N, 7.48. Found: C, 73.81; H, 5.13; N, 7.50.

Methyl 4-[1-(2-furylmethyl)-1H-indazol-3-yl]benzoate (33) and Methyl 4-[2-(2-furylmethyl)-2H-indazol-3-yl]benzoate (34)

Compound 11 (4.26 g, 0.016 mol), MeONa (2.81 g, 0.052 mol) and furfuryl chloride (15.9 mL, 0.16 mol) were allowed to react as in the preparation of compounds 14 and 15 to afford compound 33 (3.03 g, 54.7%) and compound 34 (0.42 g, 7.9%).

Compound 33: mp: 99-101° C.; MS (EI, 70 eV): m/z 332 ($M^+$); $^1$H NMR (200 MHz, DMSO-$d_6$): δ 3.87 (3H, s, $CH_3$), 5.76 (2H, s, $CH_2$), 6.40 (1H, dd, J=1.9, 3.1 Hz, H-4'), 6.55 (1H, d, J=3.1 Hz, H-3'), 7.24-7.32 (1H, m, H-5), 7.44-7.52 (1H, m, H-6), 7.56-7.57 (1H, m, H-2'), 7.85 (1H, d, J=8.5 Hz, H-7), 8.06-8.16 (5H, m, H-4, 2", 3", 5", 6"). Anal. Calcd. for $C_{21}H_{18}N_2$: C, 72.28; H, 4.85; N, 8.43. Found: C, 72.31; H, 4.86; N, 8.41.

Compound 34: mp: 140-143° C.; MS (EI, 70 eV): m/z 332 ($M^+$); $^1$H NMR (200 MHz, DMSO-$d_6$): δ 3.90 (3H, s, $CH_3$), 5.68 (2H, s, $CH_2$), 6.32 (1H, d, J=3.2 Hz, H-4'), 6.36 (1H, dd, J=1.9, 3.2 Hz, H-3'), 7.05-7.13 (1H, m, H-5), 7.26-7.33 (1H, m, H-6), 7.53-7.54 (1H, m, H-2'), 7.58-7.68 (2H, m, H-4, 7), 7.81 (2H, d, J=8.3 Hz, H-2", 6"), 8.16 (2H, d, J=8.3 Hz, H-3", 5"). Anal. Calcd. for $C_{21}H_{18}N_2$: C, 72.28; H, 4.85; N, 8.43. Found: C, 72.30; H, 4.87; N, 8.43.

4-(2-Benzyl-2H-indazol-3-yl)benzoic acid (35)

Compound 28 (1.0 g, 0.0028 mol) was suspended in 10% NaOH and reflux for 1 h. The reaction mixture was acidified with 10% HCl. The crystals formed were filtered off and recrystallized from 95% EtOH to give compound 35 (0.83 g, 90.8%).

Compound 35: mp: 159-163° C.; MS (EI, 70 eV): m/z 328 ($M^+$); $^1$H NMR (200 MHz,-DMSO-$d_6$): δ 5.71 (2H, s, $CH_2$), 6.98-7.03 (2H, m, H-2", 6"), 7.07-7.15 (1H, m, H-5), 7.21-7.35 (4H, m, H-6, 3", 4", 5"), 7.58 (1H, d, J=8.4 Hz, H-4), 7.69 (3H, d, J=8.2 Hz, H-7, 2', 6'), 8.10 (2H, d, J=8.2 Hz, H-3', 5'), 13.18 (1H, br, OH). Anal. Calcd. for $C_{21}H_{16}N_2$: C, 76.81; H, 4.91; N, 8.53. Found: C, 76.83; H, 4.93; N, 8.52.

4-[2-(4-Fluorobenzyl)-2H-indazol-3-yl]benzoic acid (36)

Compound 30 (0.5 g, 0.0013 mol) and 10% NaOH were allowed to react and treat as in the preparation of compound 35 to afford compound 36 (0.44 g, 92.6%).

Compound 36: mp: 237-239° C.; MS (EI, 70 eV): m/z 346 ($M^+$); $^1$H NMR (200 MHz, DMSO-$d_6$): δ 5.69 (2H, s, $CH_2$), 7.06-7.14 (5H, m, H-5, 2", 3", 5", 6"), 7.27-7.35 (1H, m, H-6), 7.57 (1H, d, J=8.4 Hz, H-4), 7.68 (3H, d, J=8.4 Hz, H-7, 2', 6'), 8.11 (2H, d, J=8.4 Hz, H-3', 5'). Anal. Calcd. for $C_{21}H_{15}N_2$: C, 72.82; H, 4.37; N, 8.09. Found: C, 72.83; H, 4.39; N, 8.07.

4-(2-Benzyl-2H-indazol-3-yl)-N-hydroxybenzamide (38)

To a solution of 35 (1.0 g, 0.003 mol) in $CH_2Cl_2$ (100 mL) was added $SOCl_2$ (5 mL). The mixture was refluxed for 16 h, and evaporated. The residue was washed with petroleum ether to afford 37 (0.82 g, 71.4%).

To a solution of 37 in toluene (30 mL), hydroxylamine (10 mL, 0.151 mol) was added. The mixture was reflux for 30 min and evaporated. The solids formed were filtered off and recrystallized from 50% EtOH to give compound 38 (0.41 g, 39.7%).

Compound 38: mp: 201-203° C.; MS (EI, 70 eV): m/z 343 ($M^+$); $^1H$ NMR (200 MHz, DMSO-$d_6$): δ 5.69 (2H, s, $CH_2$), 6.98-7.03 (2H, m, H-2", 6"), 7.07-7.14 (1H, m, H-5), 7.22-7.35 (4H, m, H-6, 3", 4", 5"), 7.56 (1H, d, J=8.4 Hz, H-4), 7.62-7.69 (3H, m, H-7, 2', 6'), 7.92 (2H, d, J=8.4 Hz, H-3', 5') 9.15 (1H, s, NH), 11.36 (1H, s, OH). Anal. Calcd. for $C_{21}H_{17}N_3$: C, 73.45; H, 4.99; N, 12.24. Found: C, 73.47; H, 5.02; N, 12.23.

[4-(2-Benzyl-2H-indazol-3-yl)phenyl]methanol (39)

Calcium borohydride was first prepared by stirring anhydrous calcium chloride (2.0 g, 0.018 mol) and sodium borohydride (2.0 g, 0.052 mol) in anhydrous THF (50 mL) for 4 h. Then compound 28 (1.0 g, 0.0028 mol) dissolved in THF (5 mL) was added dropwise at 25° C. The mixture was brought to reflux for 6 h, and quenched with ice water (300 mL), evaporated in vacuum, and filtered to obtain a solid product. The solid was purified by column chromatography on silica gel, elution with n-hexane/ethyl acetate (1/1) yield compound 39 (0.68 g, 76.9%).

Compound 39: mp: 148-149° C.; MS (EI, 70 eV): m/z 314 ($M^+$); $^1H$ NMR (200 MHz, DMSO-$d_6$): δ 4.59 (2H, d, J=5.7 Hz, $CH_2$), 5.34 (1H, t, J=5.7 Hz, OH), 5.65 (2H, s, N—$CH_2$), 6.99-7.06 (2H, m, H-2", 6"), 7.06-7.11 (2H, m, H-5), 7.22-7.33 (4H, m, H-6, 3", 4", 5"), 7.50-7.55 (5H, m, H-4, 2', 3', 5', 6'), 7.64 (1H, d, J=8.7 Hz, H-7). Anal. Calcd. for $C_{21}H_{18}N_2$: C, 80.23; H, 5.79; N, 8.92. Found: C, 80.25; H, 5.79; N, 8.92.

{4-[2-(2-Furylmethyl)-2H-indazol-3-yl]phenyl}methanol (40)

Compound 34 (1.0 g, 0.003 mol), calcium chloride (2.0 g, 0.018 mol) and sodium borohydride (2.0 g, 0.052 mol) were allowed to react as in the preparation of compound 39 to afford compound 40 (0.71 g, 77.3%).

Compound 40: mp: 129-130° C.; MS (EI, 70 eV): m/z 304 ($M^+$); $^1H$ NMR (200 MHz, DMSO-$d_6$): δ 4.63 (2H, d, J=5.7 Hz, $CH_2$), 5.37 (1H, t, J=5.7 Hz, OH), 5.61 (2H, s, N—$CH_2$), 6.32 (1H, d, J=3.2 Hz, H-5'), 6.39 (1H, dd, J=1.9, 3.2 Hz, H-4'), 7.01-7.24 (1H, m, H-5), 7.24-7.32 (1H, m, H-6), 7.50-7.64 (7H, m, H-3', 4, 7, 2", 3", 5", 6"). Anal. Calcd. for $C_{19}H_{16}N_2$: C, 74.98; H, 5.30; N, 9.20. Found: C, 74.97; H, 5.32; N, 9.22.

Cell Culture

Human umbilical vein endothelial cells (HUVECS) were isolated according to the protocols from Jaffe et al. and obtained from human umbilical cord veins with collagenase and cultured in 75 $cm^2$ plastic flasks in M199 containing 20% FBS, 15 μg/mL endothelial cell growth supplements (ECGs). Confirmation of their identity as endothelial cells was provided by detection of CD31 (PECAM-1), assessed by immunostaining. Experiments were conducted on HUVECs that had used in passage 2 to 5.

[$^3H$]Thymidine Incorporation Assay

Confluent HUVECs were trypsinized, suspended in DMEM supplemented with 20% FBS, and seeded at $1.0 \times 10^4$ cells per well into 96-well plates. After 24 h, the cells were washed twice with PBS and starved with 2% FBS-M199 medium for 24 h. The cells were incubated with or without indicated reagents and growth factors (VEGF; 10 ng/mL) for 24 h and harvested. Before the harvest, cells were incubated with [$^3H$]thymidine (2 μCi/mL) for 4 h, harvested with Filter-Mate (Packard), and incorporated radioactivity was determined.

In vivo Matrigel Plus Assay

Nude mice (6 weeks of age) were given s.c. injections of 500 μL of Matrigel (Becton Dickinson, Bedford, Mass.) at 4° C. with or without YC-1 and growth factor (150 ng/mL VEGF). After injection, the Matrigel rapidly formed a plug. After 7 days, the skin of the mouse was easily pulled back to expose the Matrigel plug, which remained intact. After quantitative differences were noted and photographed, hemoglobin was measured, as an indication of blood vessel formation, using the Drabkin method (Drabkin reagent kit 525, Sigma, St. Louis, Mo.). The concentration of hemoglobin was calculated from a known amount of hemoglobin assayed in parallel.

RESULTS AND DISCUSSION

Antiangiogenic Activities

In this study, 3-(4-methylphenyl)-1H-indazole (10) and five of the above mentioned $N^2$-regioisomers, namely, compounds 15, 17, 21, 25 and 26 were selected for evaluating their effects on VEGF-induced cell proliferation, on VEGF-induced tube formation of HUVECs in vitro, and on neovascular formation in vivo. The results are reported in the following.

Effect on VEGF-Induced Cell Proliferation of HUVECs

Figure 5:
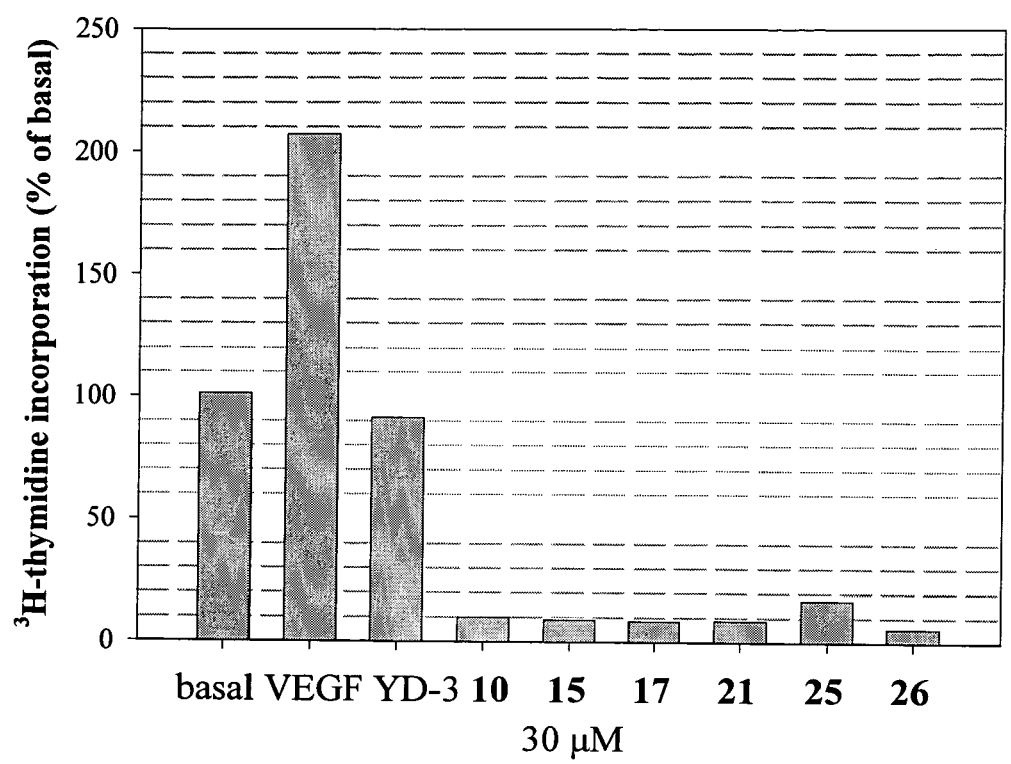
FIG. 5 shows the results of in vitro assay (inhibition of DNA synthesis). Human umbilical vein endothelial cells were incubated in the absence (basal and control) or presence of tested sample (YD-3, 10, 15, 17, 21, 25, 26) with 30 µM, and then vascular endothelial growth factor (VEGF) was added (except for basal) to induce DNA synthesis, which was detected using [$^3$H] thymidine incorporation assay.
Figure 6:
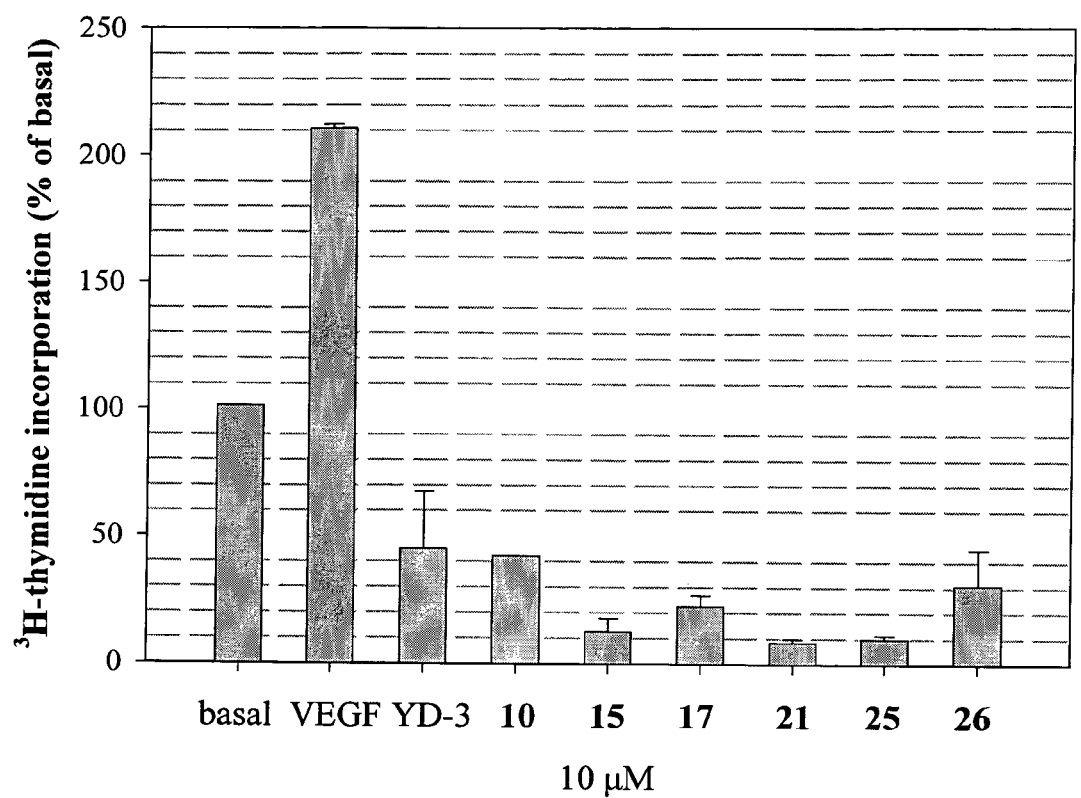
FIG. 6 shows the results of in vitro assay (inhibition of DNA synthesis). Human umbilical vein endothelial cells were incubated in the absence (basal and control) or presence of tested sample (YD-3, 10, 15, 17, 21, 25, 26) with 10 µM, and then vascular endothelial growth factor (VEGF) was added (except for basal) to induce DNA synthesis, which was detected using [$^3$H] thymidine incorporation assay. Means±S.E. (n=5) were presented.
Figure 7:
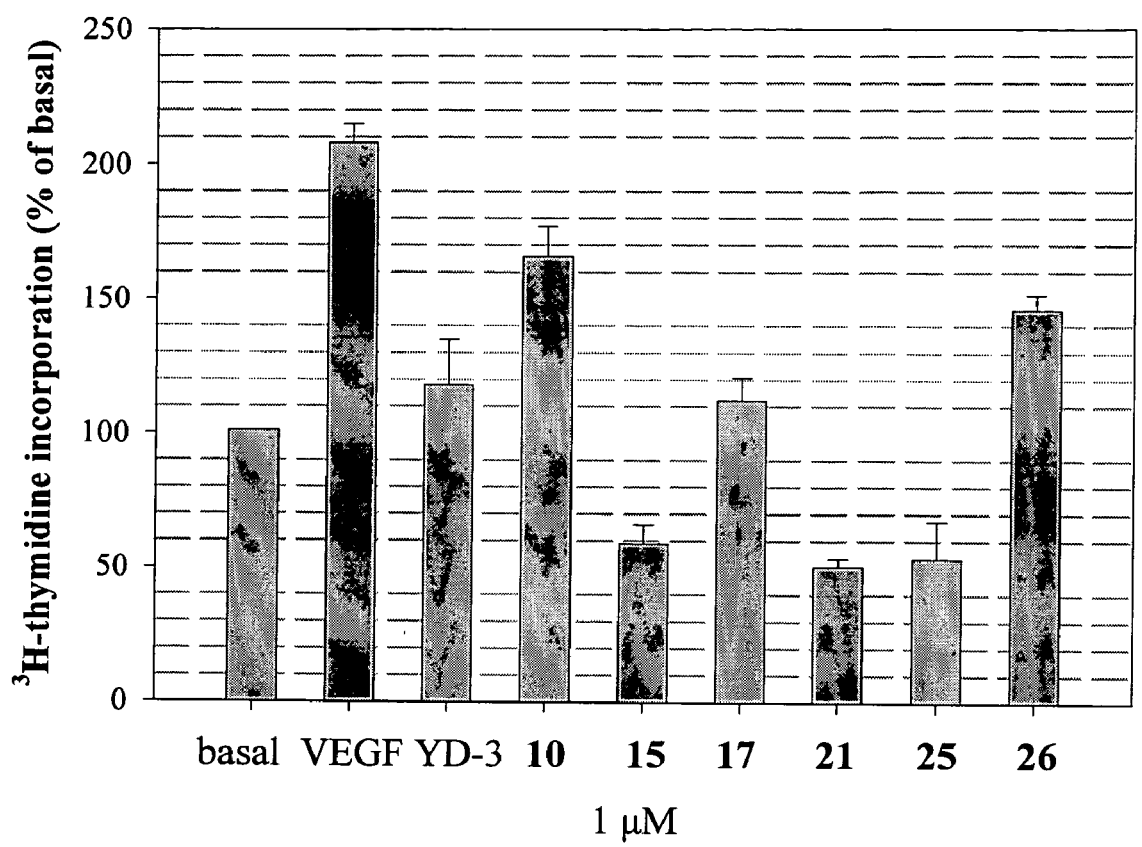
FIG. 7 shows the results of in vitro assay (inhibition of DNA synthesis). Human umbilical vein endothelial cells were incubated in the absence (basal and control) or presence of tested sample (YD-3, 10, 15, 17, 21, 25, 26) with 1 µM, and then vascular endothelial growth factor (VEGF) was added (except for basal) to induce DNA synthesis, which was detected using [$^3$H] thymidine incorporation assay. Means±S.E. (n=5) were presented.

The effect of tested compounds on VEGF-induced cell proliferation of HUVECs was assessed with the [$^3H$]thymidine incorporation assay, and the results were illustrated in FIG. 5-FIG. 7. At the concentration of 10 and 30 μM (FIG. 5, FIG. 6), all of the tested compounds (10, 15, 17, 21, 25, 26) and the positive control (YI)-3) exhibited significant inhibitory effect. When their concentration was lowered to 1 μM (FIG. 4), only compounds 15, 21 and 25 maintained better activity than positive control YD-3.

Effect on VEGF-induced Tube Formation of HUVECs

Figure 8:
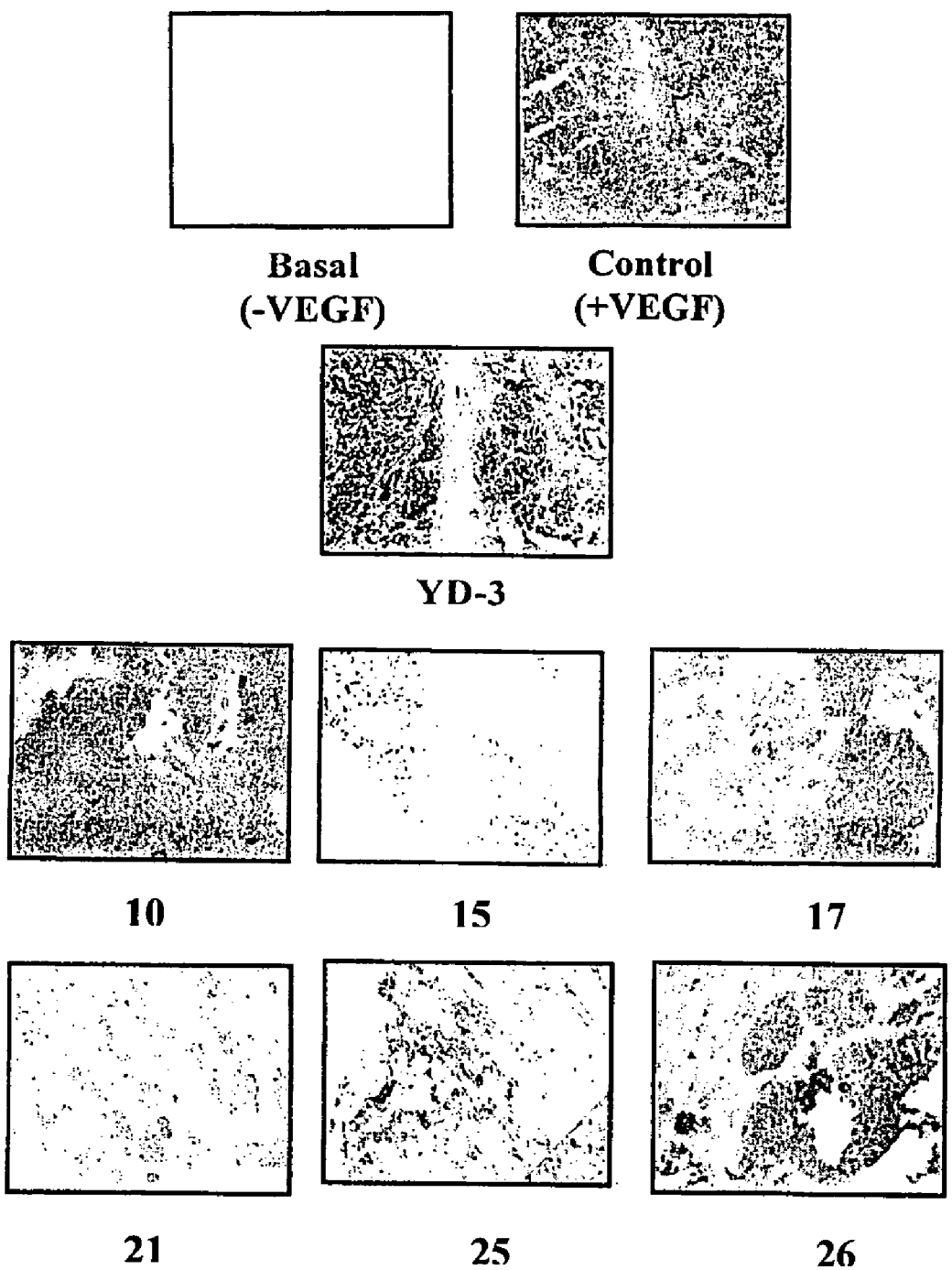
FIG. 8 show photographs of the results of in vitro assay (inhibition of tube formation). Human umbilical vein endothelial cells were cultured onto chamberslide, which was pre-coated with Matrigel (10 mg/ml). Cells were treated without (basal and control) or with tested sample (YD-3, 10, 15, 17, 21, 25, 26) and then vascular endothelial growth factor (VEGF) was added to induce tube formation. All photographs were taken at 100×magnification.

As shown in FIG. 8, without inhibitors, the treatment of HUVECs with 10 mg/ml VEGF causes the former to reorganize into capillary-like structures. For comparison, the incorporation of compounds 15, 17, 21, 25 and 26 resulted in significant blockage of VEGF-induced tube formation. Among them, compounds 15, 21 and 25 demonstrated inhibitory activity more potent than other tested compounds and YD-3.

Effect on Neovascular Formation in Vivo

Figure 9:
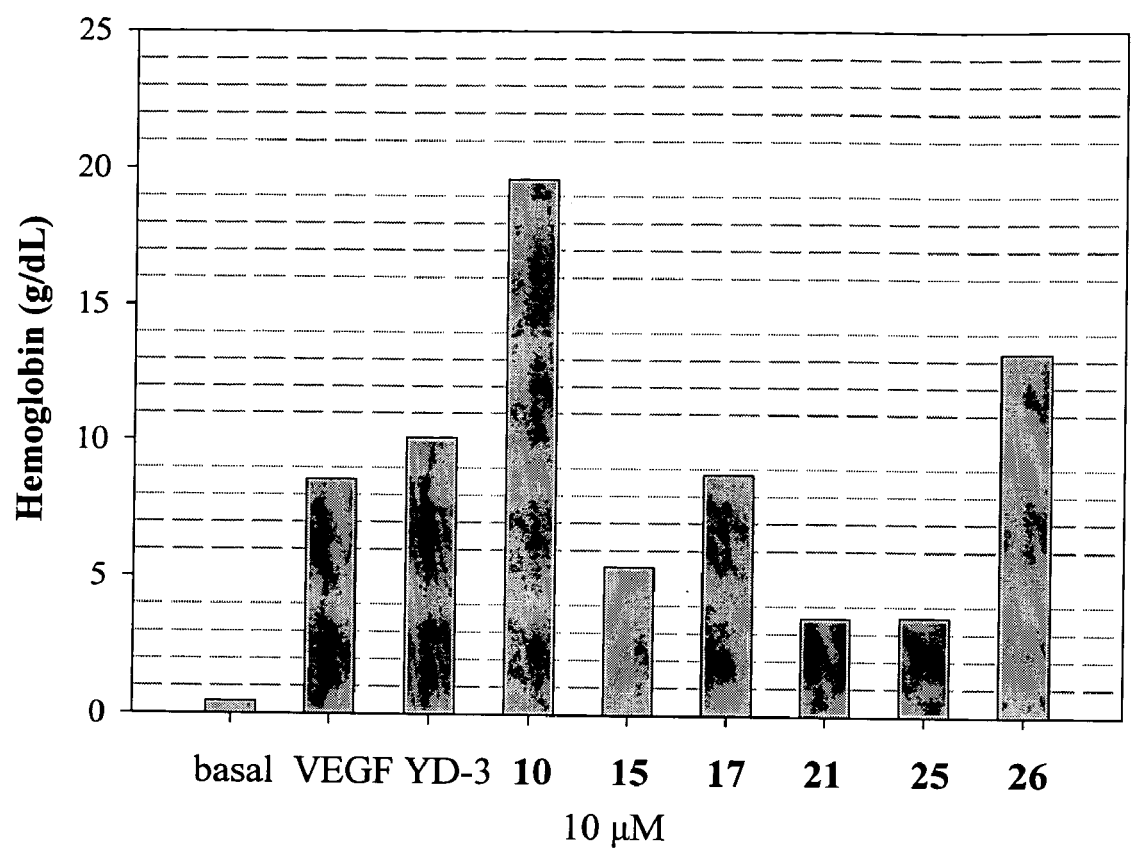
FIG. 9 shows quantitative analysis of angiogenic effect. Nude mice were subcutaneously injected with a Matrigel plug containing 150 ng/ml vascular endothelial growth factor (VEGF). Vehicle or tested sample (YD-3, 10, 15, 17, 21, 25, 26) was orally administered into the mice. After a seven-day administration, the animals were euthanized and the plugs were cut of the mice for the measurement of angiogenic effect using the hemoglobin concentration as the parameter by means of a hemoglobin detection kit (Sigma). Means±S.E. (n=3) were presented.

The in vivo Matrigel plug assay was used in this study to determine quantitative the anti-angiogenic effect of tested compounds. As shown in FIG. 9, all of five $N^2$-derivatives (15, 17, 21, 25, 26) demonstrated significant anti-angiogenic activities. Among them, 15, 21 and 25 showed superior potency than the positive control YD-3.

Analysis of the anti-angiogenic activity of our tested compounds led to the important finding that the introduction of Cl, $CH_3$, or $OCH_3$ groups into the para-position of the $N^2$-benzyl group of the tested indazoles is significantly beneficial for their anti-angiogenic activity. These three potent anti-angiogenic active compounds (15, 21, 25) are worthy of further investigation.

REFERENCES (1) C. C. Wu, S. W. Huang, T. L. Hwang, S. C. Kuo, F. Y. Lee and T. M. Teng. YD-3, a novel inhibitor of protease-induced platelet activation, *Br. J. Pharmacol.* 130, 1289-1296 (2000).

(2) F. Y. Lee, J. C. Lien, L. J. Huang, T. M. Huang, S. C. Tsai, C. M. Teng, C. C. Wu, F. C. Cheng and S. C. Kuo. Synthesis of 1-benzyl-3-(5-(hydroxymethyl-2-frryl)indazole analogues as novel antiplatelet agents. *J. Med. Chem.* 44, 3746-3749 (2001).

(3) C. C. Wu, T. L. Hwang, C. H. Liao, S. C. Kuo, F. Y. Lee, C. Y Lee and C. M. Teng. Selective inhibition of protease-activated receptor 4-dependent platelet activation by YD-3, *Thrombo. Haemost.* 87, 1026-1033 (2002).

(4) C. C. Wu, T. L. Huang, C. H. Liao, S. C. Kuo, F. Y. Lee and C. M. Teng. The role of $PAR_4$ in thrombin-induced thromboxane production in human platelet. *Thrombo. Haemost.* 90, 299-308 (2003).

What is claimed is:

1. A compound having the following formula:

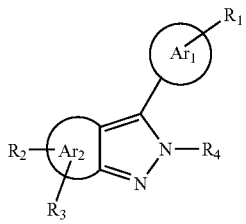

wherein
$Ar_1$ is phenyl;
$Ar_2$ is benzene;
$R_1$ is H, carboxyl, C1-C6 alkyloxycarbonyl, halocarbonyl, hydroxyl C1-C6 alkyl,

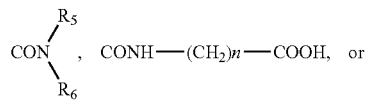

-continued

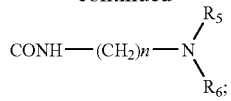

$R_2$ and $R_3$ independently are H, Cl, F, Br, OH, O—R,

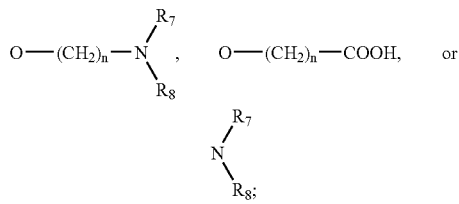

$R_4$ is $(CH_2)_n$—Ar;
wherein $R_5$, $R_6$, $R_7$, $R_8$, $R_9$ and R independently are H, halogen, hydroxyl, or C1-C6 alkyl; Ar is C6-14 aryl; furyl; halogen, C1-C6 alkyl or C1-C6 alkoxyl substituted C6-14 aryl; or halogen, C1-C6 alkyl or C1-C6 alkoxyl substituted furyl; and
n=1-6.

2. The compound as defined in claim 1, wherein Ar is phenyl, halophenyl, methyiphenyl or methoxyphenyl.

3. The compound as defined in claim 1, wherein $R_2$ and $R_3$ are hydrogen.

4. The compound as defined in claim 1, wherein $R_1$ is carboxyl, C1-C6 alkyloxycarbonyl, hydroxyl C1-C6 alkyl,

wherein $R_5$ and $R_6$ independenly are H, hydroxyl, or C1-C6 alkyl.

5. The compound according to claim 4, wherein $R_1$ is carboxyl or C1-C6 alkyloxycarbonyl.

6. The compound according to claim 1, wherein Ar is C6-14 aryl.

7. The compound according to claim 1, wherein Ar is halogen, C1-C6 alkyl, or C1-C6 alkoxyl substituted C6-14 aryl.

8. The compound according to claim 2, wherein $R_1$ is carboxyl or C1-C6 alkyloxycarbonyl.

9. The compound according to claim 8, wherein $R_2$ and $R_3$ are hydrogen.

* * * * *